US00PP25667P2

(12) United States Plant Patent
Tuinier

(10) Patent No.: US PP25,667 P2
(45) Date of Patent: Jun. 30, 2015

(54) ***GASTERIA* PLANT NAMED 'ROYAL WOLFGANG'**

(50) Latin Name: ***Gasteria* hybrid**
Varietal Denomination: Royal Wolfgang

(71) Applicant: Wander Durk Tuinier, Krimpen a/d IJssel (NL)

(72) Inventor: Wander Durk Tuinier, Krimpen a/d IJssel (NL)

(73) Assignee: Wander Tuinier BV, Krimpen a/d IJessel (NL)

( * ) Notice: Subject to any disclaimer, the term of this patent is extended or adjusted under 35 U.S.C. 154(b) by 137 days.

(21) Appl. No.: 13/987,978

(22) Filed: Sep. 20, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Anne Grunberg

(57) ABSTRACT

A new cultivar of *Gasteria* plant named 'Royal Wolfgang' that is characterized by dark green leaves with grey-green spots on the inner surface, white spots on the outer surface and margins with white teeth.

1 Drawing Sheet

Botanical classification: *Gasteria* hybrid.
Variety denomination: 'ROYAL WOLFGANG'.

BACKGROUND OF THE INVENTION

The present invention relates to a new and distinct cultivar of *Gasteria* plant botanically known as *Gasteria* hybrid and hereinafter referred to by the cultivar name 'Royal Wolfgang'.

'Royal Wolfgang' was discovered as a naturally occurring leaf mutation of *Gasteria* hybrid 'WT10' (U.S. Plant Pat. No. 23,622). 'Royal Wolfgang' was discovered in May of 2011 in a population of *Gasteria* 'WT10' plants grown from tissue culture in a greenhouse in a cultivated area of Sappemeer, The Netherlands.

Asexual reproduction of the new cultivar 'Royal Wolfgang' first occurred by tissue culture in January of 2013 in Deroose, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Gasteria* cultivar 'Royal Wolfgang'. These traits in combination distinguish 'Royal Wolfgang' as a new and distinct cultivar apart from other existing known varieties of *Gasteria*.

1. *Gasteria* 'Royal Wolfgang' exhibits dark green leaves with grey-green spots on the inner surface, white spots on the outer surface and margins with white teeth.

The closest comparison cultivar is the parent plant *Gasteria* 'WT10'. Royal Wolfgang' is distinguishable from 'WT10' by the following characteristics:

1. *Gasteria* 'Royal Wolfgang' exhibits leaves that are darker green in color than the leaves of 'WT10'.
2. *Gasteria* 'Royal Wolfgang' exhibits leaves with larger diameter white spots on the outer surface than the white spots on the outer surface of 'WT10'.

3. *Gasteria* 'Royal Wolfgang' exhibits finely denticulate leaf margins with white teeth. In comparison, the leaf margins of 'WT10' are denticulate with green teeth.

*Gasteria* 'Royal Wolfgang' can be compared to *Gasteria* 'Green Star'. Royal Wolfgang' is distinguishable from 'Green Star' by the following characteristics:

1. *Gasteria* 'Royal Wolfgang' exhibits leaves that are darker green in color than the leaves of 'Green Star'.
2. *Gasteria* 'Royal Wolfgang' exhibits leaves with white spots on the outer surface. The leaves of 'Green Star' have green spots on the outer surface.
3. *Gasteria* 'Royal Wolfgang' exhibits leaves that are wider in width than the leaves of 'Green Star'.

BRIEF DESCRIPTION OF THE DRAWING

The accompanying photographs illustrate the distinguishing traits of *Gasteria* 'Royal Wolfgang'.

Figure 1:
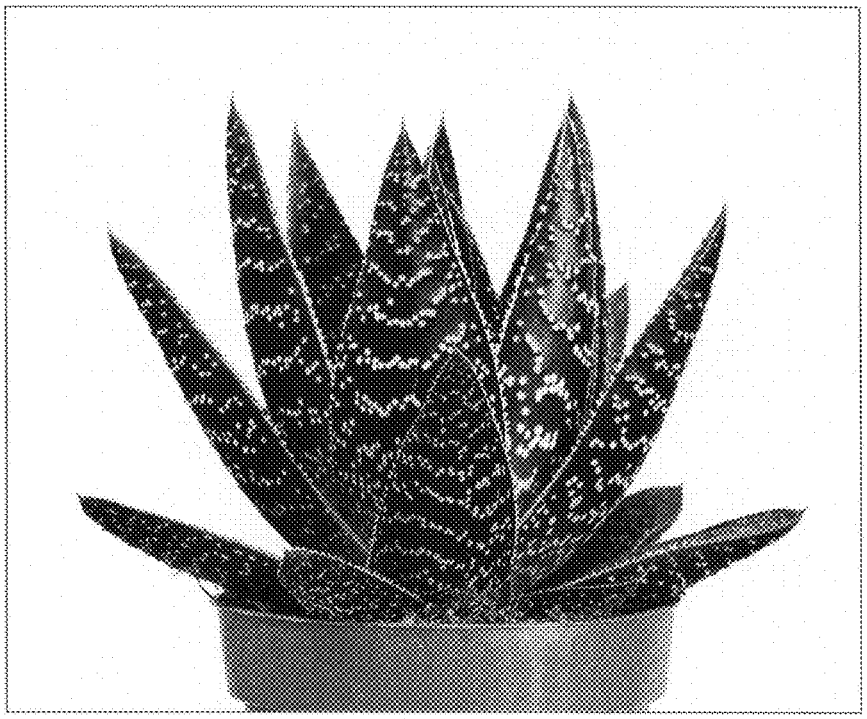
FIG. 1 shows an overall view of an 11 month old plant.
Figure 2:
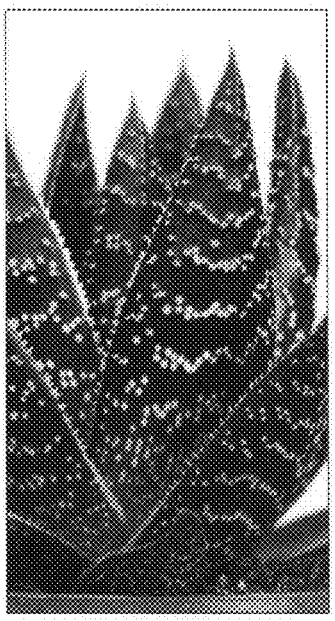
FIG. 2 shows an enlarged view of the leaves.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Gasteria* cultivar named 'Royal Wolfgang'. Data was collected in Sappemeer, The Netherlands from 11 month plants grown in a glass greenhouse in 10.5 cm. diameter containers. The time of year was July and the temperature range was 18-24 degrees Centigrade during the day and 16-20 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Royal Wolfgang' has not been tested under all possible conditions and phenotypic differences may be observed with variations in environmental, climatic, and cultural conditions, however, without any variance in genotype.

Botanical classification: *Gasteria hybrid* 'Royal Wolfgang'.

Annual or perennial: Perennial.

Parentage: 'Royal Wolfgang' is a naturally occurring leaf mutation of *Gasteria* 'WT10'.

Plant type: Potted plant.

Vigor: Moderate.

Growth habit: Upright.

Plant shape: Basal rosette.

Suitable container size: 9 cm. or larger pots.

Plant height: Average 12.0 cm. in height.

Plant width: Average 14.5 cm. in width.

Low temperature tolerance: 3° Centigrade.

High temperature tolerance: 45° Centigrade.

Propagation: Tissue culture.

Growth rate: Approximately 0.5 cm. per month.

Time to initiate roots in summer: 2 weeks.

Time to initiate roots in winter: 4 weeks.

Crop time: Approximately 15 weeks.

Root system: Fine and fibrous.

Branching: No lateral branches, basal rosette of leaves grow from the base.

Foliage:

*Leaf arrangement*.—Basal rosette.

*Compound or single*.—Single.

*Number of leaves per plant*.—Average 22.

*Leaf shape*.—Lanceolate.

*Leaf apex*.—Apiculate.

*Leaf base*.—Broad cuneate.

*Leaf length*.—Average 10.5 cm.

*Leaf width*.—Average 3.5 cm.

*Leaf thickness*.—Average 0.9 cm. at mid-section.

*Texture*.—Glossy, moderately muricate (both surfaces).

*Pubescence*.—Absent.

*Leaf margin*.—Finely denticulate.

*Venation pattern*.—No veins visible.

*Young leaf color* (*upper surface*).—N137B with muricate dots 192B and margin teeth 192B.

*Young leaf color* (*lower surface*).—N137A with muricate dots 192D and margin teeth 192D.

*Mature leaf color* (*upper surface*).—147A with muricate dots 192D and margin teeth NN155D.

*Mature leaf color* (*lower surface*).—147A with muricate dots N155B and margin teeth NN155D.

*Durability of foliage to stress*.—High.

Flowers: None observed to date.

Fruit and Seeds: None observed to date.

Disease and pest resistance: Disease and pest resistance has not been observed.

The invention claimed is:

1. A new and distinct variety of *Gasteria* plant named 'Royal Wolfgang' as described and illustrated.

* * * * *